(12) United States Patent
Spiegel

(10) Patent No.: US 12,189,212 B2
(45) Date of Patent: Jan. 7, 2025

(54) EYEWEAR COMPRISING A VARIABLE OPTICAL FILTER SYSTEM AND METHODS FOR THE SYSTEM AND EYEWEAR

(71) Applicant: ESSILOR INTERNATIONAL, Charenton-le-Pont (FR)

(72) Inventor: Daniel Spiegel, Singapore (SG)

(73) Assignee: Essilor International, Charenton-le-Pont (FR)

( * ) Notice: Subject to any disclaimer, the term of this patent is extended or adjusted under 35 U.S.C. 154(b) by 655 days.

(21) Appl. No.: 17/310,304

(22) PCT Filed: Mar. 5, 2020

(86) PCT No.: PCT/EP2020/055812
§ 371 (c)(1),
(2) Date: Jul. 27, 2021

(87) PCT Pub. No.: WO2020/178372
PCT Pub. Date: Sep. 10, 2020

(65) Prior Publication Data
US 2022/0137435 A1    May 5, 2022

(30) Foreign Application Priority Data

Mar. 6, 2019   (EP) ..................................... 19305257

(51) Int. Cl.
*G02C 11/00*    (2006.01)
*G02C 5/00*     (2006.01)
*G02C 7/10*     (2006.01)

(52) U.S. Cl.
CPC .............. *G02C 11/10* (2013.01); *G02C 5/008* (2013.01); *G02C 7/10* (2013.01)

(58) Field of Classification Search
CPC .......... G02C 11/10; G02C 5/008; G02C 7/10; G02C 7/101; A61H 2201/0157; A61H 2201/1604; A61H 5/00; A61F 9/023
(Continued)

(56) References Cited

U.S. PATENT DOCUMENTS 4,279,474 A    7/1981 Belgorod
5,452,026 A    9/1995 Marcy, III
(Continued)

FOREIGN PATENT DOCUMENTS

CN    104207876    8/2016
EP    2 927 738    10/2015
(Continued)

OTHER PUBLICATIONS

International Search Report for PCT/EP2020/055812 dated May 14, 2020, 5 pages.
(Continued)

*Primary Examiner* — Tuyen Tra
(74) *Attorney, Agent, or Firm* — NIXON & VANDERHYE

(57) ABSTRACT

An eyewear, including a first receptacle and a second receptacle; a first lens element received in the first receptacle; and a light sensor configured to detect incident light and provide a sensor signal based on the detected incident light. The eyewear further includes an analysis module. The analysis module is operably coupled to the light sensor to receive the sensor signal from the light sensor, and operably coupled to the variable optical filter structure to provide a control signal to the variable optical filter structure. The analysis module is configured to control the optical state of the variable optical filter structure thereby adjusting an illuminance ratio of light transmitted by the first lens element to light transmitted at a position of the second recep-
(Continued)

tacle. Further provided is a method for adjusting a variable optical filter system for an eyewear, and a method and computer program for controlling the eyewear.

17 Claims, 9 Drawing Sheets

(58) Field of Classification Search
USPC .................................................. 351/41, 158
See application file for complete search history.

(56) References Cited

U.S. PATENT DOCUMENTS

2013/0215376 A1    8/2013  Guo et al.
2018/0210236 A1    7/2018  Peloux et al.

FOREIGN PATENT DOCUMENTS

| WO | 92/10130 | 6/1992 |
| WO | 2014/045035 | 3/2014 |

OTHER PUBLICATIONS

Written Opinion of the ISA for PCT/EP2020/055812 dated May 14, 2020, 9 pages.

EYEWEAR COMPRISING A VARIABLE OPTICAL FILTER SYSTEM AND METHODS FOR THE SYSTEM AND EYEWEAR

CROSS-REFERENCE TO RELATED APPLICATIONS

This application is the U.S. national phase of International Application No. PCT/EP2020/055812 filed Mar. 5, 2020 which designated the U.S. and claims priority to EP 19305257.8 filed Mar. 6, 2019, the entire contents of each of which are hereby incorporated by reference.

BACKGROUND OF THE INVENTION

Field of the Invention

This disclosure relates to an eyewear including a variable optical filter system, a method for adjusting a variable optical filter system of an eyewear, a method for controlling an eyewear including a variable optical filter system, a method of correction of the human visual system, and a computer program. The eyewear may be used for the correction of the human visual system, in particular for interocular sensory imbalance.

Description of the Related Art

Interocular sensory imbalance is an inherent property of the visual system. While small interocular imbalance does not clinically manifest, large levels of this imbalance may adversely affect binocular function (e.g. stereopsis). In the more extreme cases, such as amblyopia (also known as "lazy eye"), it can also affect monocular visual processing, such as visual acuity, contrast sensitivity and other visual functions.

Scientific and clinical evidence shows that it is possible to correct amblyopia by patching the amblyopic eye, for example, by wearing a patch on the good eye thereby forcing the use of the amblyopic eye, and the stronger the interocular imbalance, the darker for the patch is needed to block more light arriving the good eye. Recent study discovers that variation on the background light intensity around the eyes may affect the interocular imbalance, thus the patch's effect on suppressing the interocular imbalance is dependent on the environment light intensity. Therefore using a fixed patch on one eye does not deliver the same amblyopia correction effect in different background light intensity, e.g. throughout a day, at different weather conditions, or indoors and outdoors conditions.

Therefore, it is desired to seek better means to enable better correction options.

SUMMARY OF THE INVENTION

A first aspect of the disclosure concerns an eyewear including a frame having an outer side and an inner side. The frame may include a first receptacle for receiving a first lens element, and a second receptacle for receiving a second lens element. The eyewear may include a first lens element received in the first receptacle, wherein the first lens element includes a variable optical filter structure. The eyewear may further include a light sensor configured to detect incident light, having an associated incident illuminance, and provide a sensor signal based on the detected incident light. The eyewear may further include an analysis module for controlling an optical state of the variable optical filter structure. The analysis module may be operably coupled to the light sensor to receive the sensor signal from the light sensor, and may be operably coupled to the variable optical filter structure to provide a control signal to the variable optical filter structure. The analysis module may be configured to control the optical state of the variable optical filter structure thereby adjusting a target illuminance ratio (TR) which is dependent on the sensor signal, The target illuminance ratio (TR) is the ratio between a first illuminance ($I_{t1}$) of light transmitted by the first lens element from the outer side to the inner side of the frame and a second illuminance ($I_{t2}$) of light transmitted from the outer side to the inner side of the frame at a position of the second receptacle.

According to various embodiments, the eyewear may further include a communication module configured to receive an electronic message transmitted for example by a communication terminal, which may be external to the eyewear.

The electronic message comprises a set of adjustment data to adjust the analysis module. The set of adjustment data may comprise at least one parameter of a functional relationship including an incident illuminance and a target illuminance ratio (TR) between a first illuminance ($I_{t1}$) and a second illuminance ($I_{t2}$).

According to an embodiment the analysis module takes into consideration the illuminance measured by the light sensor provided onto the eyewear as the electronical message providing a relationship function based on the measured incident illuminance According to various embodiments, the analysis module may be configured to generate the control signal by applying a functional relationship including an incident illuminance as input variable, and wherein the incident illuminance or a correspondent value of the incident illuminance is provided by the sensor signal.

A second aspect of the disclosure concerns a method for adjusting a variable optical filter system for an eyewear, for example for an eyewear according to the first aspect. The method for adjusting may include providing an electronic message by a communication terminal. The communication terminal may be external to the eyewear. The electronic message may include a set of adjustment data. The method for adjusting may further include transmitting the electronic message from the communication terminal and receiving the electronic message with a communication module of the eyewear. The method for adjusting may further include configuring, with the set of adjustment data, a functional relationship between an incident illuminance and a target illuminance ratio (TR) between a first illuminance ($I_{t1}$) and a second illuminance ($I_{t2}$). The first illuminance ($I_{t1}$) is an illuminance of light transmitted by a first lens element of the eyewear, and the second illuminance ($I_{t2}$) is an illuminance transmitted at an eyewear's receptacle position for receiving a second lens element of the eyewear.

A third aspect of the disclosure concerns a method for controlling an eyewear, for example, an eyewear according to the first aspect or an eyewear according to the first aspect configured by the method according to the second aspect. The eyewear may include a frame having an outer side and an inner side. The frame may include a first receptacle and a second receptacle. The eyewear may include a first lens element received in the first receptacle. The first lens element may include a variable optical filter structure. The frame may include a light sensor for providing a sensor signal based on a detected incident light detected by the light sensor. The frame may further include an analysis module. The method for controlling may include receiving the sensor signal from the light sensor by the analysis module, and providing a control signal from the analysis module to the variable optical filter structure, for controlling an optical state of the variable optical filter structure. The analysis module may be configured to control the optical state of the variable optical filter structure thereby adjusting a target illuminance ratio (TR) which is dependent on the sensor signal. The target illuminance ratio (TR) is the ratio between a first illuminance ($I_{t1}$) of light transmitted by the first lens element from the outer side to the inner side of the frame and a second illuminance ($I_{t2}$) of light transmitted from the outer side to the inner side of the frame at a position of the second receptacle. The set of adjustment data comprises data which may represent a plurality of interocular imbalance values for different illuminances. The set of adjustment data may include at least one parameter of the functional relationship. The set of adjustment data may include an optical property of the second lens element, for example a neutral optical density value, or a transmittance.

A fourth aspect of the disclosure concerns a method of correction of the human visual system, in particular for interocular sensory imbalance. The method of correction may use an eyewear, for example, an eyewear according to the first aspect or an eyewear according to the first aspect configured by the method according to the second aspect. The eyewear may include a frame having an outer side and an inner side. The frame may include a first receptacle and a second receptacle. The eyewear may include a first lens element received in the first receptacle. The first lens element may include a variable optical filter structure. The frame may include a light sensor for providing a sensor signal based on a detected incident light detected by the light sensor. The frame may further include an analysis module. The method for controlling may include receiving the sensor signal from the light sensor by the analysis module. The method for controlling may include providing a control signal from the analysis module to the variable optical filter structure, for controlling an optical state of the variable optical filter structure. The analysis module may be configured to control the optical state of the variable optical filter structure thereby adjusting a target illuminance ratio (IR) which is dependent on the sensor signal. The target illuminance ratio (TR) is the ratio between a first illuminance ($I_{t1}$) of light transmitted by the first lens element from the outer side to the inner side of the frame and a second illuminance ($I_{t2}$) of light transmitted from the outer side to the inner side of the frame at a position of the second receptacle. The set of adjustment data comprises data may represent a plurality of interocular imbalance values for different illuminances. The set of adjustment data may include at least one parameter of the functional relationship. The set of adjustment data may include an optical property of the second lens element, for example a neutral optical density value, or a transmittance.

The method for controlling may include, prior receiving the sensor signal from the light sensor by the analysis module, receiving an electronic message for example transmitted by a communication terminal, which may be external to the eyewear. The electronic message comprises a set of adjustment data to adjust the analysis module. The set of adjustment data may comprise at least one parameter of a functional relationship including an incident illuminance and a target illuminance ratio (TR) between a first illuminance ($I_{t1}$) and a second illuminance ($I_{t2}$). A fifth aspect of the disclosure concerns a computer program comprising instructions to cause the eyewear according to various embodiments, to execute the method steps of the method for controlling an eyewear and/or the method of correction.

According to various embodiments, the target illuminance ratio is smaller than 1 and may be adjustable in a range from 0.0001 to 0.95.

According to various embodiments, the variable optical filter structure may include an electrochromic layer. According to various embodiments, the variable optical filter structure may include a liquid crystal layer.

According to various embodiments, the light sensor may be adapted to detect light illuminances at least in the range from 1 lux to 50000 lux, for example from 20000 to 50000 lux.

According to various embodiments, the eyewear may further include a second lens element received in the second receptacle, wherein the second illuminance (It2) is an illuminance of light transmitted by the second lens element from the outer side to the inner side of the frame. The second lens element may include a second variable optical filter structure; wherein the analysis module may be further operably coupled to the second variable optical filter structure to provide a second control signal to the second variable optical filter structure for controlling an optical state of the second variable optical filter structure.

BRIEF DESCRIPTION OF THE DRAWINGS

Embodiments of the invention will now be described, by way of example only, and with reference to the following drawings in which.

Figure 1A:
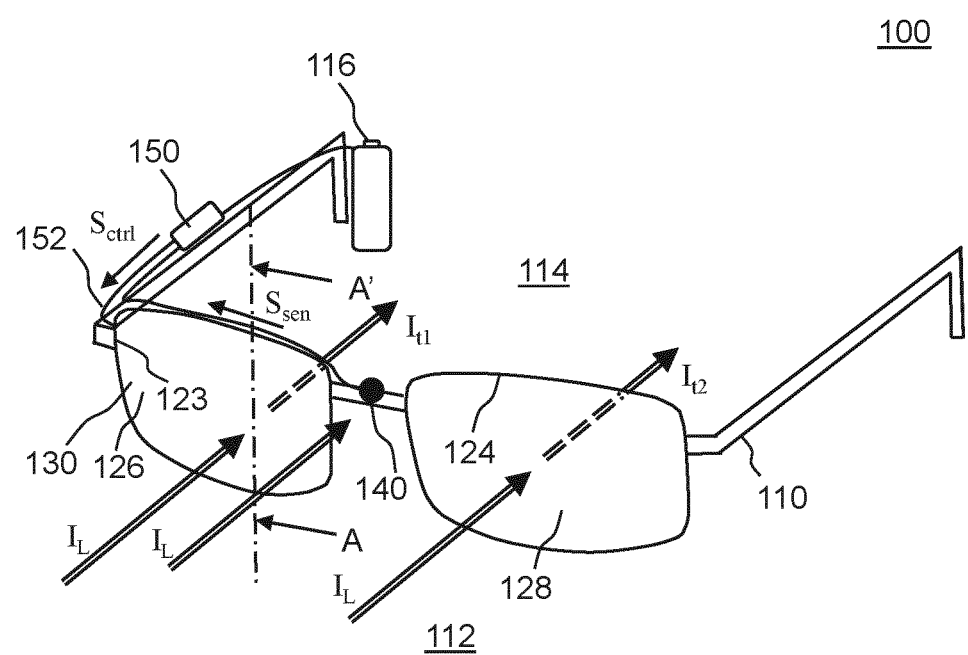
FIG. 1A shows an eyewear 100, in accordance with various embodiments.

The figures are of schematic nature and elements therein may be of different scale or positioned differently to improve readability.

DESCRIPTION OF THE PREFERRED EMBODIMENTS

In the description, which follows, the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may be embodied in a wide variety of contexts. Embodiments discussed herein are merely representative and do not limit the scope of the invention.

Various embodiments disclosed herein relate to the various aspects of the disclosure such as an eyewear including a variable optical filter system, a method for adjusting a variable optical filter system of an eyewear, a method for controlling an eyewear including a variable optical filter system, a method of correction of the human visual system, and a computer program.

Embodiments and explanations thereof disclosed in connection with one embodiment may be applicable to other embodiments. For example, embodiments and explanations to the eyewear may be applicable to the method for adjusting, the method of controlling, or to the method of correction. In another example, details of the method for controlling and/or adjusting may apply to the embodiments of the eyewear which eyewear, such as the analysis module or the communication module, may be configured accordingly.

The term "eyewear", according to various embodiments, may refer to an object to be wear on/in relation to the eye, for example spectacles.

The term "lens element", for example the first lens element or the second lens element, according to various embodiments, may refer to a lens for an eyewear, which may or may not have corrective power.

The term "receptacle", according to various embodiments, may refer to a means for receiving a lens element. For example a rim, or a strap, or a combination thereof.

As used herein, the term "and/or" includes any and all combinations of one or more of the associated listed items.

While the examples disclosed herein use the light illuminance, for example in incident illuminance or incident illuminance ranges, the skilled person in the art would understand that other physical quantities may be used, for example by carrying out the appropriate conversion between the illuminance and another form of intensity, such as a different luminous intensity, a radiant intensity, or a photocurrent of a photodetector.

Figure 1B:
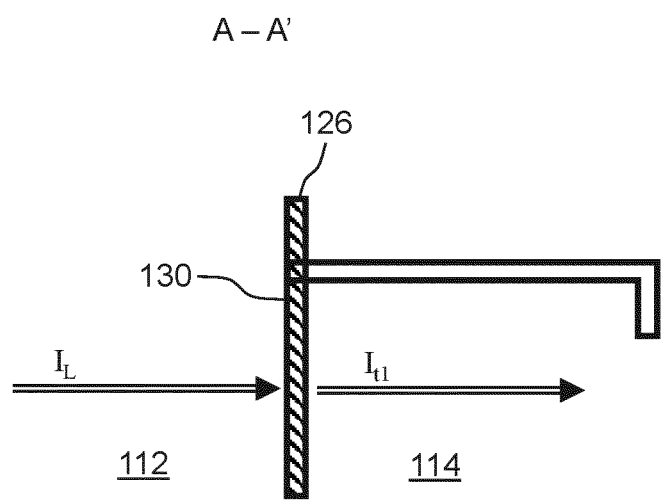
FIG. 1B is a cross-section view of cross section A-A' from the eyewear 100 of FIG. 1A.

FIG. 1A shows an eyewear 100, including a frame 110 having an outer side 112 and an inner side 114. FIG. 1B is a cross-section view of cross section A-A' from the eyewear 100 of FIG. 1A. The frame 110 may include a first receptacle 122 and a second receptacle 124. The eyewear 100 may include a first lens element 126 received in the first receptacle 122, wherein the first lens element 126 comprises a variable optical filter structure 130. According to some embodiments, the variable optical filter structure may include an electrochromic layer. Alternatively, the variable optical filter structure may include a liquid crystal layer. The frame 110 may include other elements, for example, the frame 110 may include a bridge connecting to the first receptacle 122 and the second receptacle 124. The frame 110 may also include a pair of earpieces. The frame 110 may further include a power source 116.

In one example, the liquid crystal layer may include at least one cell comprising a transparent liquid crystal formulation between two transparent supports, at least one (for example both) of the transparent supports comprises a transparent electrode. The liquid crystal layer may include a polarizer. According to one embodiment, the transparent liquid crystal formulation placed between the two transparent supports may be in phase organization which is dependent on the applied electrical field applied to the transparent electrode(s), so that for at least two different electrical fields, two different phase organizations may be obtained, which together with the polarizer, may provide at least two different optical states of the variable optical filter structure, for example at least two different neutral density filter states. Exemplary materials for the transparent liquid crystal formulation may include twisted nematic liquid crystal materials and/or further include dichroic dies, for example, as provided by AlphaMicron, Inc.

In one example, the electrochromic layer may include at least one cell comprising an electrochromic formulation between two transparent supports, at least one (for example both) of the transparent supports comprises a transparent electrode. Thus, the electrochromic layer and the transparent electrode(s) may be arranged as an arrangement of layers. According to one embodiment, the electrochromic formulation placed between the two transparent supports may include chemical redox states which are dependent on the applied electrical field (and correspondent current) applied to the transparent electrode(s), so that for at least two different electrical fields, two different redox states may be obtained, for which the electrochromic formulation has different absorption coefficients. The different absorptions may be used to provide at least two different optical states of the variable optical filter structure, for example at least two different neutral density filter states. The electrochromic layer may include solid and/or liquid layers. Further, an electrolyte may be included in at least one of the layers of the arrangement of layers. For example, the electrochromic layer may include a solid layer of WO3 and a conductive polymer layer, for example a polyaniline or a polyaniline derivative.

The eyewear 100 may include a light sensor 140 configured to detect incident light with an incident illuminance $I_L$ and provide a sensor signal $S_{Sen}$ based on the detected incident illuminance $I_L$. For example, the light sensor 140 may be coupled to the frame 110, for example, mechanically integrated in the frame 110. The incident light may be the ambient light. According to some embodiments, the light sensor may be adapted to detect light illuminances at least in the range from 1 lux to 50000 lux.

The eyewear 100 may include an analysis module 150 for controlling an optical state of the variable optical filter structure 130. The analysis module 150 may be any electronic circuit, for example, including a microcontroller. The electronic circuit may include analog and/or digital inputs and outputs. The analysis module 150 may be operably coupled to the light sensor 140 to receive the sensor signal $S_{Sen}$ from the light sensor 140, for example, the eyewear may include conductors which may electrically connect the light sensor 140 to the analysis module 150. The analysis module 150 may be operably coupled to the variable optical filter structure 130 to provide a control signal $S_{ctrl}$ to the variable optical filter structure 130, for example, the eyewear may include conductors which may electrically connect the analysis module 150 to the optical state of the variable optical filter structure 130. The analysis module 150 may be configured to control the optical state of the variable optical filter structure 130, thereby adjusting a target illuminance ratio TR which is dependent on the sensor signal $S_{Sen}$. The power source may be included in the analysis module.

The target illuminance ratio TR is the ratio between a first illuminance $I_{t1}$ of light transmitted by the first lens element 126 from the outer side 112 to the inner side 114 of the frame 110 and a second illuminance $I_{t2}$ of light transmitted from the outer side 112 to the inner side 114 of the frame 110 at a position of the second receptacle 124. The direction of transmission of light is from the outer side 112 to the inner side 114 of the frame 110 as shown in FIG. 1B. Thus, if a user is wearing the frame, the direction would be essentially in the direction of the user's eye.

The target illuminance ratio may be given by $TR=I_{t1}/I_{t2}$. The target illuminance ratio TR may be dimensionless, for example, due to the division of [lux]/[lux]. Given an incident light, e.g. detected in the form of illuminance $I_L$, or a corresponding/converted value thereof, the analysis module 150 may determine a respective illuminance ratio for said given incident illuminance and determine the target illuminance ratio TR to provide a control signal $S_{ctrl}$ to the variable optical filter structure 130 so to obtain the desired first illuminance $I_{t1}$ (for example using $I_{t1}=TR \cdot I_{t2}$) of light transmitted by the first lens element 126 from the outer side 112 to the inner side 114 of the frame 110. In some embodiments, the second illuminance $I_{t2}$, of light transmitted from the outer side 112 to the inner side 114 of the frame 110 at a position of the second receptacle 124, may be equal or substantially equal to the incident illuminance $I_L$, for example when the second receptacle 124 does not include any lens, or the second receptacle 124 includes a second lens element 128 which is essentially transparent. According to various embodiments, the target illuminance ratio TR is smaller than 1 and may be adjustable in a range from 0.0001 to 0.95.

Figure 2:
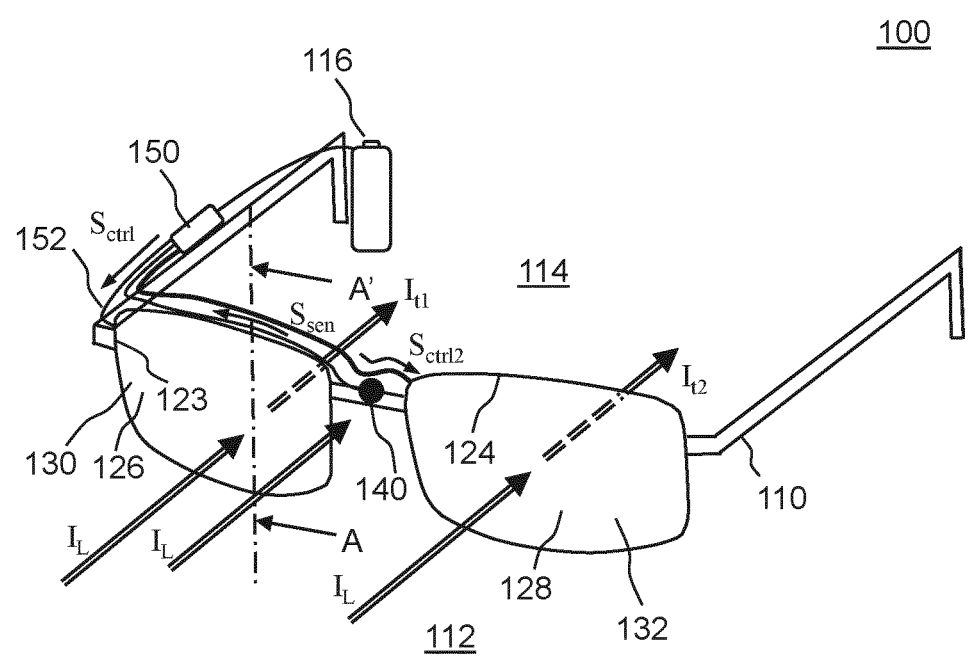
FIG. 2 is an example of an eyewear 100, in accordance with various embodiments, wherein the second lens element 128 includes a second variable optical filter structure 132.

FIG. 2 is an example of an eyewear 100, in accordance with various embodiments, wherein the second lens element 128 includes a second variable optical filter structure 132.

According to various embodiments, the eyewear 100 may further include a second lens element 128 received in the second receptacle 124. In such case, the second illuminance $I_{t2}$ is the illuminance of light transmitted by the second lens element 128 from the outer side 112 to the inner side 114 of the frame 110.

According to various embodiments, the second lens element 128 may further include a second variable optical filter structure 132. In such case, the analysis module 150 may be further operably coupled to the second variable optical filter structure 132 to provide a second control signal $S_{ctrl2}$ to the second variable optical filter structure 132 for controlling an optical state of the second variable optical filter structure 132. The provision of a second variable optical filter structure allows for a higher dynamic range, and more freedom for adjusting the target interocular balance.

Figure 3A:
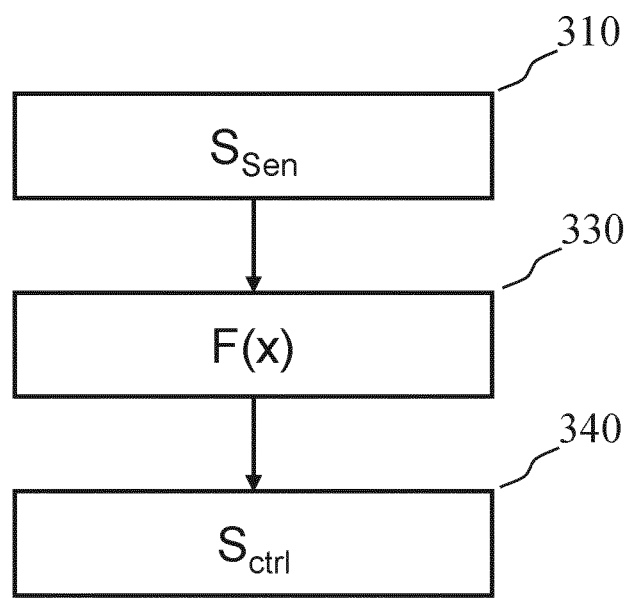
FIG. 3A shows a flowchart 300 showing how a control signal is provided by the functional relationship from the sensor signal, in accordance with some embodiments.

FIG. 3A shows a flowchart 300 showing how a control signal is provided by the functional relationship from the sensor signal, in accordance with some embodiments.

According to various embodiments, the analysis module may be configured to generate the control signal by applying a functional relationship F(x) including an incident illuminance $I_L$ ($x=I_L$) as input variable, and wherein the incident illuminance $I_L$ or a correspondent value of the incident illuminance $I_L$ is provided by the sensor signal $S_{Sen}$. As shown in FIG. 3A, a sensor signal $S_{Sen}$ may be provided, for example acquired by measuring the incident light, in a first step 310, and the sensor signal $S_{Sen}$ may be provided to functional relationship F(x) in step 330. The sensor signal $S_{Sen}$ may be in the unit of lux, thus representing the incident illuminance. Using the output of the functional relationship F(x), the control module may provide a control signal $S_{ctrl}$ in step 340.

Figure 3B:
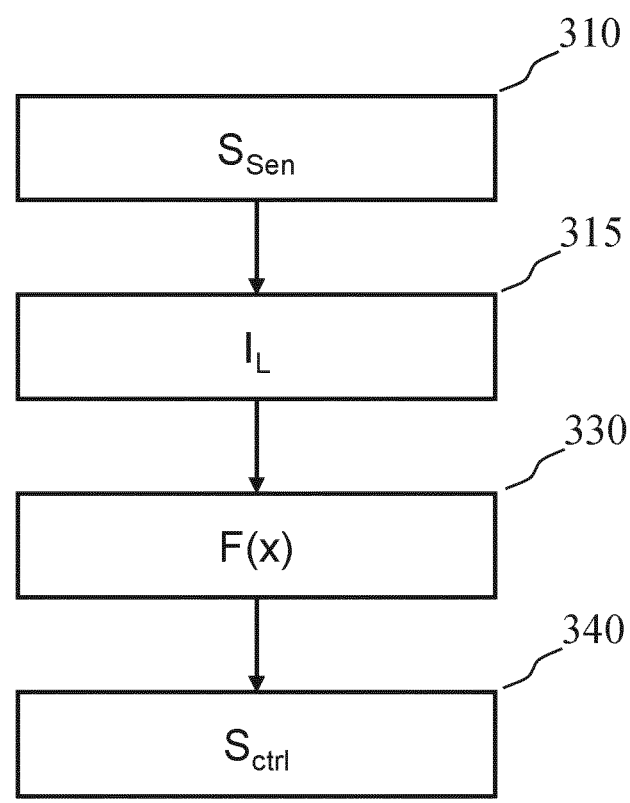
FIG. 3B shows a flowchart 301 showing how a control signal is provided by the functional relationship receiving an incident illuminance which may be converted from the sensor signal, in accordance with some embodiments.

FIG. 3B shows a flowchart 301 showing how a control signal is provided by the functional relationship receiving an incident illuminance which may be converted from the sensor signal, in accordance with some embodiments. As shown in FIG. 3B, a sensor signal $S_{Sen}$ may be provided, for example in the form of a photocurrent, for example acquired by measuring the incident light, in a first step 310. The sensor signal $S_{Sen}$ may be converted to illuminance units in a step 315, to represent the incident illuminance $I_L$. Step 315, may be carried out, for example, by the analysis module, and the analysis module may thus be configured accordingly. The incident illuminance $I_L$ may be provided to functional relationship F(x) in step 330. Using the output of the functional relationship F(x), the control module may provide a control signal $S_{ctrl}$ in step 340.

Referring to FIGS. 3A and 3B for illustration purposes, various embodiments also relate to a method of controlling the eyewear, the method including: receiving the sensor signal from the light sensor by the analysis module, and providing a control signal from the analysis module to the variable optical filter structure, for controlling an optical state of the variable optical filter structure. The method further includes, controlling, by the analysis module, the optical state of the variable optical filter structure thereby adjusting a target illuminance ratio (TR) which is dependent on the sensor signal, wherein the target illuminance ratio (TR) is the ratio between a first illuminance ($I_{t1}$) of light transmitted by the first lens element from the outer side to the inner side of the frame and a second illuminance ($I_{t2}$) of light transmitted from the outer side to the inner side of the frame at a position of the second receptacle.

Various embodiments also concern a computer program comprising instructions to cause the eyewear according to various embodiments to execute the method steps of the method for controlling an eyewear and/or the method of correction.

Figure 4:
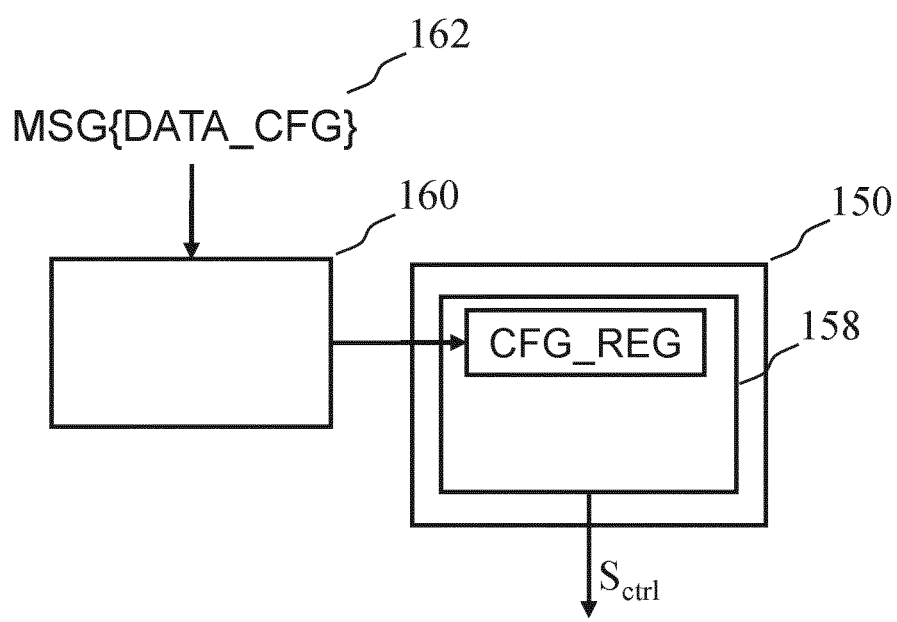
FIG. 4 is a schematic showing details of the communication module 160 and its connection to the analysis module 150, in accordance with various embodiments.

According to various embodiments, the eyewear may further include a communication module configured to receive an electronic message including a set of adjustment data to adjust the analysis module. FIG. 4 is a schematic showing details of the communication module 160 and its connection to the analysis module 150, in accordance with various embodiments. FIG. 4 shows a communication module 160 operably coupled to the analysis module 150. The communication module 160 is configured to receive an electronic message 162 (MSG), which may contain a set of adjustment data DATA_CFG. The adjustment data DATA_CFG may be transmitted to the communication module 160 and serve as configuration for the communication module 160, for example, the adjustment data DATA_CFG may include a table with a plurality of illuminance ratios (IR), wherein each illuminance ratio of the plurality of illuminance ratios may be associated to an incident illuminance range or a corresponding/converted value thereof.

The table may also be a single row or single column table of an output (such as illuminance ratios IR1 . . . IRn, for n greater than 2) for which the index n (which may be, e.g., a position in the table) may be the input (for example incident illuminance ranges IL1 . . . ILn). In another example, the associated incident illuminance ranges may be pre-defined in the analysis module 150. In yet another example, the adjustment data DATA_CFG may include a table with a plurality of illuminance ratios and a plurality of associated incident illuminance ranges. Instead of, or in addition to, of a plurality of illuminance ratios (IR), the table could include a plurality of interocular imbalance ratios which may be converted, for example in a separate step, to a target illuminance ratio.

An illuminance ratio of the plurality of illuminance ratios may be determined, for example, as $IR=1-(IOI+A)$; wherein IOI is Interocular Imbalance (a ratio with values $0 \leq IOI \leq 1$, preferably $0<IOI<1$), and A is a constant (for example $0 \leq A \leq 1$), for example when 0 is zero target illuminance ratio may compensate out the interocular imbalance, when A is greater than 0, the target illuminance ratio may overcompensate the interocular imbalance.

Alternatively or in addition to the adjustment data DATA_CFG including a table with a plurality of illuminance ratios, the adjustment data DATA_CFG may include a table with a plurality of interocular imbalance ratios (e.g., each ratio for a different incident illuminance range), and the plurality of illuminance ratios may be determined from the interocular imbalance ratios.

The interocular imbalance may be determined for a subject with known methods, for example the using the dichoptic random dot task.

Figure 5A:
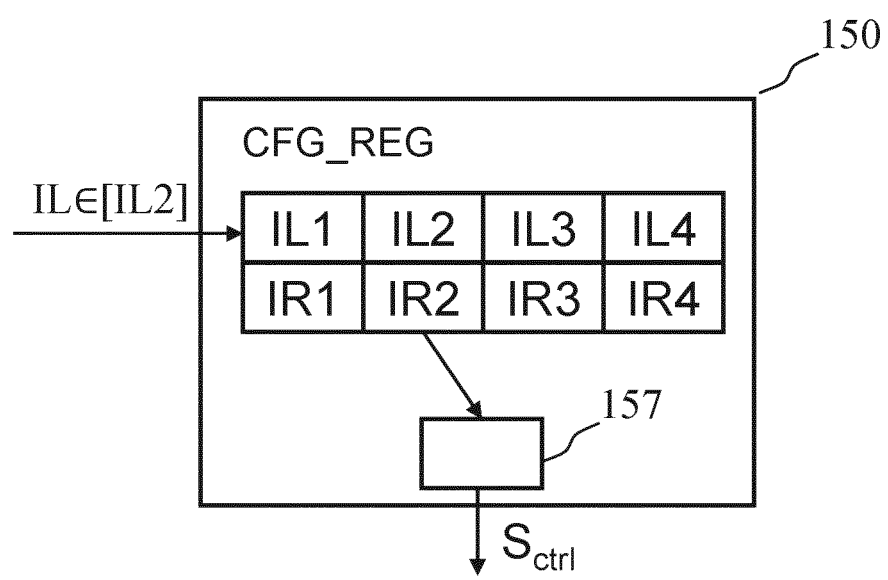
FIG. 5A shows an example of an implementation of a functional relationship in an analysis module 150, in accordance with various embodiments.

FIG. 5A shows an example of an analysis module 150 which is configured to control the optical state of the variable optical filter structure 130 with the control signal $S_{ctrl}$. The analysis module is configured with a functional relationship F(x), which may for example include a configuration register CFG_REG. The configuration register CFG_REG may be configured with adjustment data DATA_CFG as previously described, and may include the illuminance ratios IR1 . . . IR4. While 4 illuminance ratios are shown, the disclosure is not limited thereto and the illuminance ratios may be IR1 . . . IRn, for n greater than 2, for example x=5. The configuration register CFG_REG may further include the incident illuminance ranges IL1 . . . IL4, alternatively or in addition, the incident illuminance ranges IL1 . . . IL4 may be an integral part of the analysis module 150, for example pre-programmed in the table or included in the software's algorithm of the analysis module 150. While 4 incident illuminance ranges are shown, the disclosure is not limited thereto and the incident illuminance ranges may be IL1 . . . ILn=y, for y greater than 2, for example y=n=5. Having a sensor signal $S_{Sen}$ as input, for example in the form of an incident illuminance $I_L$, the analysis module may determine into which one of incident illuminance ranges IL1, IL2, IL3, and IL4 the incident illuminance $I_L$ (the sensor signal $S_{Sen}$ may be converted into illuminance if necessary) is contained and provide a respective target illumination ratio. In the example of FIG. 5A, it is shown for illustration purposes, that $I_L \in [IL2]$, meaning that the $I_L$ is contained in the range IL2, which results in the target illumination ratio being determined to be equal to IR2. The target illumination ratio (e.g. IR2) may be further processed (157) so that the control signal $S_{ctrl}$ is generated, which control signal $S_{ctrl}$ may be provided to the variable optical filter structure 130. The further processing 157, may be, for example, the transformation from a digital signal into an analog signal and/or signal amplification.

Figure 5B:
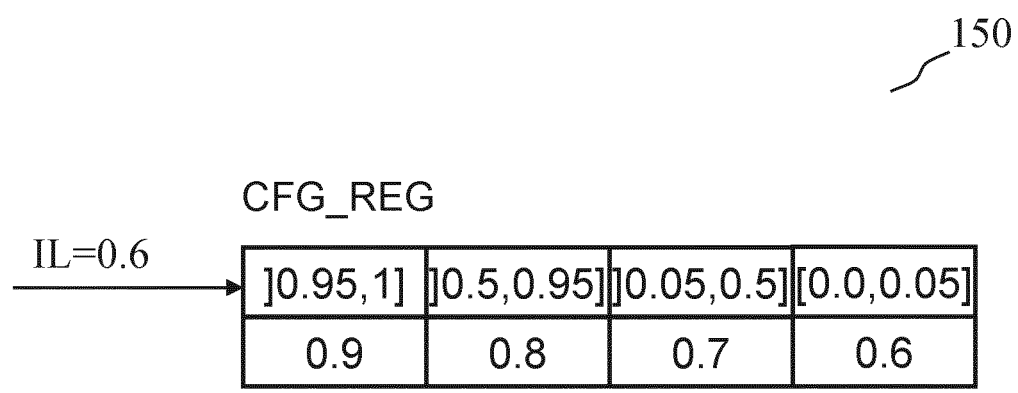
FIG. 5B is a table of exemplary values for the configuration register CFG_REG of FIG. 5A.

FIG. 5B shows exemplary values for the configuration register CFG_REG of FIG. 5A. In FIG. 5B, the light intensity ranges are represented, for illustration purposes, as values between 0 and 1 (endpoints included), wherein 1 represents a maximum pre-determined illuminance, for example 50000 lux, and 0 represents the dark condition (without any light). In FIG. 5B the exemplary ranges are as follows: IL1=]0.95,1]; IL2=]0.5,0.95]; IL3=]0.05,0.5], and IL4=[0.0,0.05]. The square brackets refer to the mathematical representation of intervals, wherein the square brackets include the end-points and the parenthesis does not include the end-points. Alternatively, the illuminance ranges ILx may include a single value, for example, IL1=1, IL2=0.9, IL3=0.1, and IL4=0.01, and the ranges associated with each value may be determined by an algorithm or circuit of the analysis module.

In FIG. 5B, the illuminance ratios are represented, for illustration purposes, as IR1=0.9, IR2=0.8, IR3=0.7, and IR4=0.6. For an incident illuminance $I_L$ of 0.6, which is in the range of IL2 (]0.5,0.95]), the functional relationship F(x) determines the target illuminance ratio TR to be IR2 (0.8). The analysis module is configured to provide a corresponding control signal $S_{ctrl}$, for example, by converting and/or amplifying an electronic signal corresponding to the determined target illuminance ratio IR.

According to the functional relationship F(x), if the incident illuminance $I_L$ is decreased, the target illuminance ratio TR becomes smaller. The target illuminance ratio TR may be smaller if the wearer is in a dark environment with a dark background light than if the wearer is in a bright light environment The functional relationship F(x) is exemplified in several drawing as table, for example a correspondence table. The table may be a single row or single column table of an output (such as illuminance ratios IR1 . . . IRn, for n greater than 2) for which the index (also named as position or cell in the table) may be the input (for example incident illuminance ranges IL1 . . . ILn). The input may be further processed. The output may be further processed. The functional relationship F(x) (e.g. the table) may be implemented in software, for example in a program for a microcontroller. While the functional relationship F(x) is shown in the form of a table, the present disclosure is not limited thereto, the functional relationship F(x) may be implemented as a function according to a software algorithm, or for example with an analog electronic circuit.

Figure 6:
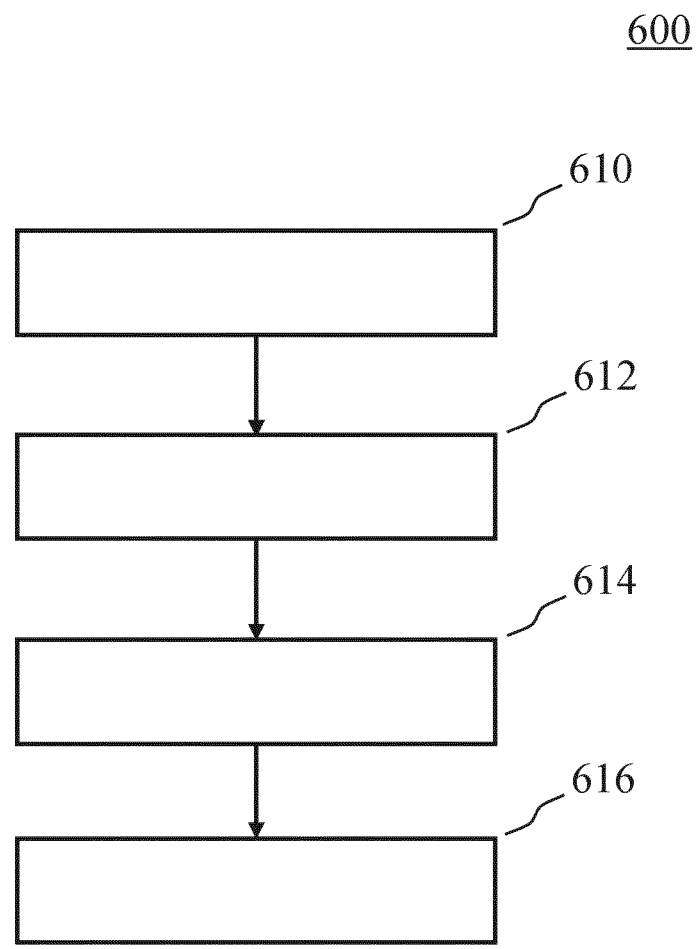
FIG. 6 shows a flowchart of a method 600 for adjusting a variable optical filter system for an eyewear in accordance with various embodiments.

FIG. 6 shows a flowchart of a method 600 for adjusting a variable optical filter system for an eyewear in accordance with various embodiments. The method 600 for adjusting a variable optical filter system may include providing, in a step 610, an electronic message by a communication terminal. The communication terminal may be external to the eyewear. For example the communication terminal may be a computer terminal for which information can be input so that the electronic message with a set of adjustment data can be generated. The method 600 for adjusting a variable optical filter system may further include transmitting the electronic message from the communication terminal in a step 612, and receiving the electronic message with a communication module of the eyewear in a step 614 (transmission and reception may occur essentially at the same time).

The method 600 for adjusting a variable optical filter system may further include, in a step 616, configuring, with the set of adjustment data, a functional relationship between an incident illuminance and a target illuminance ratio (TR), wherein TR refers to the ratio between a first illuminance ($I_{t1}$) and a second illuminance ($I_{t2}$). The first illuminance ($I_{t1}$) is an illuminance of light transmitted by a first lens element of the eyewear, and the second illuminance ($I_{t2}$) is an illuminance transmitted at an eyewear's receptacle position for receiving a second lens element of the eyewear, as previously described. The eyewear may be an eyewear as described in the various embodiments herein.

According to various embodiments, the set of adjustment data may include data representing a plurality of interocular imbalance values for different illuminances. In this case, instead of transmitting the adjustment data DATA_CFG including a table with a plurality of illuminance ratios (as previous explained), the DATA_CFG may include a table with the plurality of interocular imbalance values for different illuminances and the corresponding illuminance ratios IR1 . . . IRn may be determined, for example, calculated, by the analysis module 150.

According to various embodiments, the set of adjustment data may include at least one parameter of the functional relationship. For example, the parameters may be offset or an angular coefficient in the functional relationship. For example, the functional relationship may further include an amplification factor for the control signal $S_{ctrl}$, as parameter.

The functional relationship may change for the eyewear wearer. The wearer with the eyewear may be measured periodically on the illuminance ratio TR at different level of incident illuminance $I_L$ as well as measured on the suppression of the interocular imbalance for the wearer. The adjustment data could be obtained based on the measurement results, which is used to adjust the functional relationship for the specific wearer.

According to some embodiments, the set of adjustment data comprises a second illuminance $It_2$ of the second lens element. For example, the second lens element may have a certain transmittance, for example an averaged transmittance over the visible range, which may be used by the analysis module, for example, as input variable in the functional relationship, for determining the corresponding target illuminance ratio and generating the control signal $S_{ctrl}$. In one example, the second lens element may be a neutral density filter.

In the case where the transmittance of the second receptacle is substantially 1, for example, when no second lens element or a substantial transparent second lens element is included in the second receptacle, the second illuminance It2 of the second lens element (for example, illuminance incident on the respective eye (behind the second receptacle) of a subject wearing the eyewear) is essentially the same as the incident illuminance $I_L$.

Various embodiments concern a method of correction of the human visual system, in particular for interocular sensory imbalance. The method of correction may use an eyewear, for example, an eyewear as described in accordance with various embodiments. With the eyewear in accordance to various embodiments, it is possible to penalize the good eye for different incident illuminances (e.g. different ambient light intensities) so that the interocular illuminance difference shifts the ocular dominance towards the other eye, which is the eye with higher illuminance Since the interocular imbalance is considered as a function of the incident illuminance, an improved correction can be provided to a subject, for example under diverse illuminance conditions, which may be effective, for example under bright sun, as well as under early morning or evening sunshine.

The invention claimed is:

1. An eyewear, comprising:
   a frame having an outer side and an inner side, and comprising a first receptacle and a second receptacle;
   a first lens element received in the first receptacle, wherein the first lens element comprises a variable optical filter structure;
   a light sensor configured to detect incident light and provide a sensor signal based on the detected incident light; and
   an analysis module configured to control an optical state of the variable optical filter structure, the analysis module being operably coupled to the light sensor to receive the sensor signal from the light sensor, and operably coupled to the variable optical filter structure to provide a control signal to the variable optical filter structure,
   wherein the analysis module is configured to control the optical state of the variable optical filter structure thereby adjusting a target illuminance ratio which is dependent on the sensor signal, the target illuminance ratio being the ratio between a first illuminance of light transmitted by the first lens element from the outer side to the inner side of the frame and a second illuminance of light transmitted from the outer side to the inner side of the frame at a position of the second receptacle, and
   wherein the target illuminance ratio is adjustable in range from 0.0001 to 0.95.

2. The eyewear of claim 1, further comprising a communication module configured to receive an electronic message comprising a set of adjustment data to adjust the analysis module.

3. A method for adjusting a variable optical filter system for the eyewear according to claim 2, the method comprising:
   providing an electronic message by a communication terminal, wherein the communication terminal is external to the eyewear, the electronic message comprising a set of adjustment data;
   transmitting the electronic message from the communication terminal and receiving the electronic message with a communication module of the eyewear; and
   configuring, with the set of adjustment data, a functional relationship between an incident illuminance and a target illuminance ratio between the first illuminance and the second illuminance,
   wherein the first illuminance is an illuminance of light transmitted by the first lens element of the eyewear, and the second illuminance is an illuminance transmitted at a receptacle position of the eyewear to receive the second lens element of the eyewear.

4. The method of claim 3, wherein the set of adjustment data comprises data representing a plurality of interocular imbalance values for different illuminances.

5. The method of claim 3, wherein the set of adjustment data comprises at least one parameter of the functional relationship.

6. The method of claim 3, wherein the set of adjustment data comprises a transmittance value of the second lens element.

7. The eyewear of claim 2, wherein the analysis module is configured to generate the control signal by applying a functional relationship including an incident illuminance of the incident light as input variable, and
   wherein the incident illuminance or a correspondent value of the incident illuminance is provided by the sensor signal.

8. The eyewear of claim 2, wherein the variable optical filter structure comprises an electrochromic layer or a liquid crystal layer.

9. The eyewear of claim 1, wherein the analysis module is configured to generate the control signal by applying a functional relationship including an incident illuminance of the incident light as input variable, and
   wherein the incident illuminance or a correspondent value of the incident illuminance is provided by the sensor signal.

10. The eyewear of claim 1, wherein the variable optical filter structure comprises an electrochromic layer or a liquid crystal layer.

11. The eyewear of claim 1, wherein light sensor is configured to detect light the illuminances of the incident light at least in the range from 1 lux to 50,000 lux.

12. The eyewear of claim 11, wherein the light sensor is configured to detect light illuminances of the incident light at least in the range from 20,000 to 50,000 lux.

13. The eyewear of claim 1, further comprising:
a second lens element received in the second receptacle, wherein the second illuminance is an illuminance of light transmitted by the second lens element from the outer side to the inner side of the frame.

14. The eyewear of claim 13, wherein the second lens element comprises a second variable optical filter structure, wherein the analysis module is further operably coupled to the second variable optical filter structure to provide a second control signal to the second variable optical filter structure to control an optical state of the second variable optical filter structure.

15. A non-transitory computer-readable medium on which is stored a computer program comprising instructions that, when executed by an analysis module, cause the analysis module in the eyewear of claim 1 to execute a method comprising:
receiving the sensor signal from the light sensor by the analysis module; and
providing a control signal from the analysis module to the variable optical filter structure, to control an optical state of the variable optical filter structure;
controlling, by the analysis module, the optical state of the variable optical filter structure thereby adjusting a target illuminance ratio which is dependent on the sensor signal, wherein the target illuminance ratio (TR) is the ratio between a first illuminance of light transmitted by the first lens element from the outer side to the inner side of the frame and a second illuminance of light transmitted from the outer side to the inner side of the frame at a position of the second receptacle,
wherein the target illuminance ratio is adjustable in range from 0.0001 to 0.95.

16. A method for controlling an eyewear including a frame having an outer side and an inner side, a first receptacle, a second receptacle, a first lens element received in the first receptacle, a light sensor configured to provide a sensor signal based on a detected incident light detected by the light sensor, and an analysis module, the first lens element including a variable optical filter structure, the method comprising:
receiving the sensor signal from the light sensor by the analysis module; and
providing a control signal from the analysis module to the variable optical filter structure, to control an optical state of the variable optical filter structure; and
controlling, by the analysis module, the optical state of the variable optical filter structure thereby adjusting a target illuminance ratio which is dependent on the sensor signal, the target illuminance ratio being the ratio between a first illuminance of light transmitted by the first lens element from the outer side to the inner side of the frame and a second illuminance of light transmitted from the outer side to the inner side of the frame at a position of the second receptacle, and
wherein the target illuminance ratio is adjustable in range from 0.0001 to 0.95.

17. The method for controlling according to claim 16, wherein, prior to receiving the sensor signal from the light sensor by the analysis module, receiving an electronic message transmitted by a communication terminal external to the eyewear, the electronic message comprising a set of adjustment data to adjust the analysis module, the set of adjustment data comprising at least one parameter of a functional relationship including the incident illuminance and a target illuminance ratio between the first illuminance and the second illuminance.

* * * * *